United States Patent [19]

Reid

[11] Patent Number: 6,054,632
[45] Date of Patent: *Apr. 25, 2000

[54] METHOD OF MAKING MONOCLONAL ANTIBODIES USING POLYMORPHIC TRANSGENIC ANIMALS

[75] Inventor: Marion E. Reid, New York, N.Y.

[73] Assignee: New York Blood Center, Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/749,527

[22] Filed: Nov. 15, 1996

[51] Int. Cl.$^7$ .............................. A61K 48/00; C12N 5/10; C12N 5/28; C12N 15/09

[52] U.S. Cl. ................................. 800/6; 800/4; 424/93.1; 424/93.21; 424/141.1; 435/70.21; 435/70.2; 935/89; 514/2

[58] Field of Search ........................... 435/320.1, 6, 69.1, 435/375, 93.21, 70.2, 70.21; 800/2, 4, 6, 8, 18, 21, 25; 424/93.1, 141.1; 935/89, 62, 70, 93; 536/23.5; 514/2

[56] References Cited

U.S. PATENT DOCUMENTS

| | | | |
|---|---|---|---|
| 5,101,017 | 3/1992 | Rubinstein et al. | 530/388 |
| 5,198,347 | 3/1993 | Miller et al. | 435/69.1 |
| 5,541,292 | 7/1996 | Miller et al. | 530/35 |
| 5,578,714 | 11/1996 | Pogo et al. | 536/23.5 |

OTHER PUBLICATIONS

Kappel et al. "Regulating gene expression in transgenic animals," Current Opinion in Biotechnology, vol. 3: 548–553, 1992.

Jakobovits, A. "Production of fully human antibodies in transgenic mice," Current Opinion in Biotechnology, vol. 6, No. 5: 561–566, Oct. 1995.

Asok Chaudhuri, Valerie Zbrzezna, Carol Johnson, Margaret Nichols, Pablo Rubenstein, W. Laurence Marsh, and A. Oscar Pogo, "Purification and Characterization of an Erythrocyte Membrane Protein Complex Carrying Duffy Blood Group Antigenicity," (1989) *The Journal of Biological Chemistry* 264, 13770–13774.

Asok Chaudhuri, Julia Polyakova, Valerie Zbrzezna, Kenneth Williams, Subhash Gulati, and A. Oscar Pogo, "Cloning of Glycoprotein D cDNA, Which Encodes the Major Subunit of the Duffy Blood Group System and the Receptor for the Plasmodium Vivax Malaria Parasite," (1993) *Proc. Natl. Acad. Sci. USA* 90, 10793–10797.

S. Mathew, A. Chaudhuri, V.V.V.S Murty and A.O. Pogo, "Confirmation of Duffy Blood Group antigen Locus (FY) at 1q22→q23 by Fluorescence in Situ Hybridization," (1994) *Cytogenet Cell Genet* 67, 68.

Asok Chaudhuri, Valerie Zbrzezna, Julia Polyakova, A. Oscar Pogo, Joseph Hesselgesser, and Richard Horuk, "Expression of the Duffy Antigen in K562 Cells," (1994) *The Journal of Biological Chemistry* 269, 7835–7838.

Asok Chaudhuri and A. Oscar Pogo, "The Duffy Blood Group System and Malaria," (1995) *Blood Cell Biochemistry, Molecular Basis of Major Human Blood Group Antigens* 6, 243–265.

Asok Chaudhuri, Julia Polyakova, Valerie Zbrzezna, and A. Oscar Pogo, "The Coding Sequence of Duffy Blood Group Gene in Humans and Simians: Restriction Fragment Length Polymorphism, Antibody and Malarial Parasite Specificities, and Expression in Nonerythroid Tissues in Duffy–Negative Individuals," (1995) *Blood* 85, 615–621.

A.O. Pogo, A. Chaudhuri, "Duffy and Receptors for P. Vivax and Chemotactic Peptides," (1995) *TCB* 4, 269–276.

Christophe Tournamille, Yves Colin, Jean Pierre Cartron & Caroline Le Van Kim, "Disruption of a GATA Motif in the Duffy Gene Promoter Abolishes Erythroid Gene Expression in Duffy–Negative Individuals," (1995) *Nature Genetics* 10, 224–228.

Sadahiko Iwamoto, Toshinori Omni, Eiji Kajii, and Shigenori Ikemoto, "Genomic Organization of the Glycoprotein D Gene: Duffy Blood Group $Fy^a/Fy^b$ Alloantigen System is Associated with a Polymorphism at the 44–Amino Acid Residue" (1995) *Blood* 85, 622–626.

Sadahiko Iwamoto, Jianping Li, Toshinori Omi, Sigenori Ikemoto, and Eiji Kajii, "Identification of a Novel Exon and Spliced Form of Duffy mRNA That is the Predominant Transcript Both Erythroid and Postcapillary Venule Endothelium" (1996) *Blood* 87, 378–385.

*Primary Examiner*—Karen Hauda
*Attorney, Agent, or Firm*—Hoffmann & Baron, LLP

[57] ABSTRACT

The invention relates to a method for making monoclonal antibodies having pre-defined specificity for an epitope characteristic of or unique to a single form of a polymorphic protein. The method includes constructing a first transgenic animal to express a first form of a polymorphic protein encoded by a first allele of a gene encoding the protein; constructing a second transgenic animal to express a second form of the polymorphic protein encoded by a second allele of the gene encoding the protein; and immunizing the first transgenic animal with cells from the second transgenic animal expressing the second form of the polymorphic protein to induce an immune response in the first transgenic animal yielding an antibody specific for an epitope peculiar to the second form of the polymorphic protein. The invention further includes hybridoma cells secreting a monoclonal antibody specific for the second form of the protein. The invention is particularly advantageous in the context of making monoclonal antibodies and derivative reagents specifically identifying polymorphic blood group proteins, such as the Duffy gp-Fy protein.

10 Claims, 6 Drawing Sheets

FIG-3A

Sense-primer for DNA amplification →

```
CTGCAGGGGT AGATGCCCTT TCTCTCTGCT GGCCAGCTCT GCCCCTCAGT GAGAAACTTT   60
ACATATTGCT AAGATGCCTG GCCAATGAAA CAGTTCCAGA GACTTTATGT CCCCAGTAGA  120
AATATGAATA GAAATCACCC TGTGGGCAAT GGTCCCATTT AAAATATGC TGTCCCATTG   180
TCCCCTAGAG CCTACTTTAA CTTGTCAGAC CATGTATTCC ACTTCATATG CAAGAGGCAT  240
GCACTGAGCC CATAGGTGGC TAGGCAAACA CCCAATAGCT CCTGAAATG GCTTCATTAT   300
GGAGGCTCGA CAGCCACCCC AACCCTCCCA CTCTCACACT GAAACACCCA GACCTAGAGA  360
TAGCTAGACA CACCCAGACA CCCGCCAAGC CCCTCACATA CAGATATGTG CACAATGATA  420
CACAGCAAAT GTACACAGAG TTCAGTACAC ACAAAGAGCT CACGCCCACG TGCACACACC  480
CCTCAGTTGG GACAGAGTTG ACCACCACCA CCTTTCTCCC AAACACATGG CTTTGGAACT  540
GCCTTTCCTT GGATCCAGTT CAAGGGGATG GAGGAGCAGT GAGAGTCAGC CGCCCTTCCA  600
CTCCAATTTC CCAGCACCTC CCTTATCTCT GCCTCACAAG TCACCCAGCC CCCCTCTCTT  660
CCTTCCTTGT GCTTGAAGAA TCTCTCCTTG CTGGAAAGCC CCCTGTTTTC TCAATCTCCC  720
TTTCCACTTC GGTAAAATCT CTCCTTGCTG GAAAGCCCCC TGTTTTCTCA ATCTCCCTTT  780
CCACTTCGGT AAAATGCCCA CTTTCTGGTC CCCACCTTTT TCCTGAGTGT AGTCCCAACC  840
AGCCAAATCC AACCTCAAAA CAGGAAGACC CAAGGCCAGT GACCCCCATA GGCCTGAGGC  900
TTGTTGCAGG CAGTGGGCGT GGGGTAAGGC TTCCTGATGC CCCCTGTCCC TGCCCAGAAC  960
CTGATGGCCC TCATTAGTCC TTGGCTCTTA TCTTGGAAGC ACAGGCGCTG ACAGCCGTAC 1020
CAGCCCTTCT GTCTGCGGGC CTGAACCAAA CGGTGCCATG GGAACTGTC TGCACAGGGT  1080
GAGTATGGGG CCAGGCCCCA GAGTCCCTTA TCCCTATGCC CCTCATTTCC CCTGCTGTTT 1140
GCCCCTCAGT CTTTATATCT CTTCCTTTTC CTCCTCATCT TTTCTCCCTT CCTGCTTTTT 1200
TCCTCTTCCT TCAAAGTCTT TTTCCTTTTC TCCTTCCTAT GCTAGCCTCC TAGCTCCCTC 1260
TTGTGTCCCT CCCTTTGCCT TTGAGTCAGT TCCATCCTGG TCTCTTGGTG CCTTTCCTTC 1320
TGACCTTGCA CTGCTCCTCC AGCCCCAGCT GCCCTGGCTT CCCCAGGACT GTTCCTGCTC 1380
CGGCTCTTCA GGCTCCCTGC TTTGTCCTTT TCCACTGTCC GCACTGCATC TGACTCCTGC 1440
AGAGACCTTG TTCTCCCACC CGACCTTCCT CTCTGTCCTC CCCTCCCACC TGCCCCTCAG 1500
```
→ Initial codon of Duffy GP open reading frame
```
TTCCCAGGAG ACTCTTCCGG TGTAACTCTG ATGGCCTCCT CTGGGTATGT CCTCCAGGCG 1560
GAGCTCTCCC CCTCAACTGA GAACTCAAGT CAGCTGGACT TCGAAGATGT ATGGAATTCT 1620
                                                  *
TCCTATGGTG TGAATGATTC CTTCCCAGAT GGAGACTATG ATGCCAACCT GGAAGCAGCT 1680
                                  └──────── G in FY*A ────────┘ Primer for mutagenesis
GCCCCCTGCC ACTCCTGTAA CCTGCTGGAT GACTCTGCAC TGCCCTTCTT CATCCTCACC 1740
```

FIG-3B

```
AGTGTCCTGG GTATCCTAGC TAGCAGCACT GTCCTCTTCA TGCTTTTCAG ACCTCTCTTC  1800
CGCTGGCAGC TCTGCCCTGG CTGGCCTGTC CTGGCACAGC TGGCTGTGGG CAGTGCCCTC  1860
TTCAGCATTG TGGTGCCCGT CTTGGCCCCA GGGCTAGGTA GCACTCGCAG CTCTGCCCTG  1920
TGTAGCCTGG GCTACTGTGT CTGGTATGGC TCAGCCTTTG CCCAGGCTTT GCTGCTAGGG  1980
TGCCATGCCT CCCTGGGCCA CAGACTGGGT GCAGGCCAGG TCCCAGGCCT CACCCTGGGG  2040
CTCACTGTGG GAATTTGGGG AGTGGCTGCC CTACTGACAC TGCCTGTCAC CCTGGCCAGT  2100
GGTGCTTCTG GTGGACTCTG CACCCTGATA TACAGCACGG AGCTGAAGGC TTTGCAGGCC  2160
ACACACACTG TAGCCTGTCT TGCCATCTTT GTCTTGTTGC CATTGGGTTT GTTTGGAGCC  2220
AAGGGCTGA AGAAGGCATT GGGTATGGGG CCAGGCCCCT GGATGAATAT CCTGTGGGCC  2280
TGGTTTATTT TCTGGTGGCC TCATGGGGTG GTTCTAGGAC TGGATTTCCT GGTGAGGTCC  2340
AAGCTGTTGC TGTTGTCAAC ATGTCTGGCC CAGCAGGCTC TGGACCTGCT GCTGAACCTG  2400
GCAGAAGCCC TGGCAATTTT GCACTGTGTG GCTACGCCCC TGCTCCTCGC CCTATTCTGC  2460
CACCAGGCCA CCCGCACCCT CTTGCCCTCT CTGCCCCTCC CTGAAGGATG GTCTTCTCAT  2520
CTGGACACCC TTGGAAGCAA ATCCTAGTTC TCTTCCCACC TGTCAACCTG AATTAAAGTC  2580
                                    ★ Stop codon
TACACTGCCT TTGTGAAGCG GGTGGTTTCT TATTTGTCT GGGGAGAAGA AGGAGAATGG  2640
AGAGAGAGAC ATTTTTATGT CAGACTTTCT TGCCAGTGTC TGCTTCTATA GCTGGCTTGG  2700
GAAGAAGGTG AATGATGAAT AAATACCCTC AGGGTACACA GATGTTCTCT TGAGGTGTGG  2760
GGTCAGGCCA TCTCAAGGGA GAAGAGAAGA GGAACTAGAG CATGAGGGGA GTCATTAAAC  2820
CAAAAAAAC AGAAGGGATG GCTTAGCTGG AAAAAAAGCT GTTCTGGGAA GCAAATGGAA  2880
TAGGAACTCA AACTGAGAGA TAAACAGTGA AGAGTGATGA CAAAGCCCAG AGCAATACCA  2940
CCTCCCCCTG TCCAACCTGC CCAGCCTCTG TCTTCTGTCT CCTCTCTGGC TTTGTTTAGT  3000
GATTAGGACA GTGGTGGGGA AGGTGAAAGA AGCATCCCAG GGGATGTTAC TCAGTTCAGG  3060
GAACATATCA AGGTAATTTA AAAAGCCACT TCCTGGGAGT CATCTCTCCC AGGTTCCTCA  3120
GCATGACCTG AATGTGTGTG TGTGCGTGTG TGTGTGTGTG TGTACACATC TGTTTCTCGA  3180
TCTGTTAGAA TCTACCTTTA TGTTAGATGT ATGCATGTAA AAACATATGT CCACCCATGA  3240
GCTTGCATCT CTGTCAGCAC CTGAACTGCG ACACCTGTGC GTGTGCACTG ACTTTCTCA  3300
GGACCCAAAC CCCCACTCAA TTCTGCACTC ATCCCTGTTC ACAGGATATA GAATCGGGAT  3360
TTATGACTCA CTCCTTACCC AAATGAGTTT TCTTTACCCT GGTTTTTAAG CCTAGTCTTT  3420
TCTGTGTAGG ATGTGTGGAG GGAAGAAAAG ATCAAGAAGT TGTGAGGGGT GGAGAAACTT  3480
GAAGGGGGAG GCCCTGATTT GATTCATCTT CTGCTTGGAA TTC
                            ◄ Anti-sense primer for DNA amplification
```

METHOD OF MAKING MONOCLONAL ANTIBODIES USING POLYMORPHIC TRANSGENIC ANIMALS

BACKGROUND OF THE INVENTION

The invention relates to methods of making antibodies. More specifically, the invention relates to the selective production of monoclonal antibodies having predefined specificity.

Almost a century ago, the discovery of ABO blood groups by Karl Landsteiner (1901) led to the development of routine blood grouping procedures in the practice of pretransfusion testing performed today. This testing depends on agglutination resulting from the interaction between the red blood cells (RBCs) and their cognate antibodies. Historically, human-source reagents have been used for blood group antigen typing. From time to time attempts have been made to use non-human reagents for blood grouping. Injection of human RBCs to animals, such as mice and rabbits, often results in production of a mixture of antibodies which require extensive absorption or purification for use to detect a single polymorphic determinant. However, with the advent of the ability to produce monoclonal antibodies (MAbs) having predefined specificities as described in the mid-seventies (Kohler et al. 1975), and in view of the legally restricted immunization of individuals with allogeneic RBCs, a new era began in the blood typing industry.

In producing these new monoclonal antibodies, after immunization of mice with appropriate antigens (e.g., RBCs), an antibody-secreting spleen cell is isolated and fused with an "immortal cell" (a myeloma cell line), to create a hybrid cell called a "hybridoma." The resulting hybridoma uniquely secretes the antibody of interest into the culture medium, but is also immortal, thereby capable of acting as a continuous source of the antibody.

The first murine MAb-based blood typing reagent, an anti-M, was licensed by the Food and Drug Administration in 1984 and since that date, MAb reagents for ABO typing have replaced those prepared from plasma from human donors. MAbs have the advantages of unlimited supply, batch-to-batch consistency, absence of contaminating antibody specificities, and minimal biohazard risk to blood typing staff.

While efforts have been concentrated on making MAbs using the mouse hybridoma system, new techniques keep on developing. In vitro infection of human B-lymphocytes with Epstein-Barr virus (EBV) results in production of transformed, immunoglobulin-secreting lymphoblastoid cells which survive in tissue culture indefinitely and continue to secrete specific antibodies. EBV-transformed human lymphoblastoid cell lines can be fused with a mouse/human myeloma cell line to make MAbs. In this fashion, human anti-D, anti-C and anti-E have been made (Doyle et al. 1985; Crawford et al. 1983). However, the major limitation of this technique is the need for lymphocytes from recently immunized human donors. Thus, this is not an effective method for producing a broad range of blood grouping reagents.

Enriched RBC membrane proteins and synthetic peptides have also been used to immunize animals. Unfortunately, limited success has been obtained due to the inability of the animal to recognize blood group polymorphisms, or because the antigens are only expressed if the protein is embedded in the RBC membrane.

While monoclonal technology has advanced substantially and concerted efforts have been made in many institutions, it has not yet proven possible to make MAb reagents with certain specificities, notably anti-$Fy^a$ and anti-$Fy^b$. In addition, as human source material, e.g., antibodies of sufficient potency, becomes harder and harder to obtain, it is inevitable that MAb reagents will be needed to replace polyclonal reagents. It is obvious that new approaches are needed if MAbs with specificities that are not currently available are to be made.

In view of the above considerations, it is clear that existing methods for making antibodies are limited. Moreover, it is evident that existing blood typing reagents based on antibodies are limited in both quality and quantity, necessitating new sources of such reagents.

Accordingly, it is one of the purposes of this invention to overcome the above limitations in the manufacture of antibodies, by providing a method which enables designed production of antibodies, particularly monoclonal antibodies to have particular pre-defined specificities. The availability of such designer antibodies thereby enables the manufacture and production of reagents and methods of detecting expression specific proteins which are presently either difficult or even impossible to identify by conventional methods. Therefore, it is another purpose of the invention to provide a method of making a wide range of MAbs capable of use for typing blood samples, investigating functions of proteins, and developing therapeutic reagents.

SUMMARY OF THE INVENTION

It has now been discovered that these and other objectives can be achieved by the present invention, which provides a method for making an antibody, comprising:

constructing a first transgenic animal to express a first form of an exogenous polymorphic protein encoded by a first allele of a gene encoding the protein;

constructing a second transgenic animal to express a second form of the polymorphic protein encoded by a second allele of the gene encoding the protein;

immunizing the first transgenic animal with cells from the second transgenic animal expressing the second form of the polymorphic protein to induce an immune response in the first transgenic animal yielding an antibody specific for an epitope characteristic of the second form of the polymorphic protein.

The method preferably further comprises isolating from the first transgenic animal a lymphoid cell capable of producing the antibody, as well as the cell isolated thereby. More preferably, the method further comprises fusing the isolated antibody-producing lymphoid cell with an immortal cell to provide an antibody-producing hybridoma cell.

The invention, therefore, provides a method of making a hybridoma cell which produces a monoclonal antibody having specificity for an epitope uniquely identifying or characteristic of a single form of a polymorphic protein. The invention further includes the hybridoma cell produced by the method, as well as the monoclonal antibody produced by the hybridoma cell.

The method of the invention can be employed in the context of an exogenous polymorphic protein which is expressed on a cell membrane. Preferably, the polymorphic protein is a blood group protein. More preferably, the blood group protein is gp-Fy protein. It is preferred that the polymorphic protein is a human polymorphic protein.

Preferably, the first transgenic animal and the second transgenic animal are both transformed from animals of one inbred strain. It is further preferred that the first and second transgenic animals are mice.

The invention further includes a hybridoma cell, preferably one that cannot routinely be made by conventional or standard methods known in the art. The hybridoma cell is produced by a method comprising:

constructing a first transgenic animal to express a first form of an exogenous polymorphic protein encoded by a first allele of a gene encoding the protein;

constructing a second transgenic animal to express a second form of the polymorphic protein encoded by a second allele of the gene encoding the protein;

immunizing the first transgenic animal with cells from the second transgenic animal expressing the second form of the polymorphic protein to induce an immune response in the first transgenic animal yielding an antibody specific for an epitope characteristic of the second form of the polymorphic protein;

isolating from the first transgenic animal a lymphoid cell capable of producing the antibody; and fusing the antibody-producing lymphoid cell with an immortal cell to provide an antibody-producing hybridoma cell.

The hybridoma cell is preferably capable of producing an antibody specific for an epitope characteristic of a form of a polymorphic protein which is a blood group protein, more preferably being capable of producing an antibody specific for an epitope characteristic a form of gp-Fy protein.

The invention also includes an antibody specific for an epitope characteristic of one form of a polymorphic protein, produced by a method comprising:

constructing a first transgenic animal to express a first form of an exogenous polymorphic protein encoded by a first allele of a gene encoding the protein;

constructing a second transgenic animal to express a second form of the polymorphic protein encoded by a second allele of the gene encoding the protein;

immunizing the first transgenic animal with cells from the second transgenic animal expressing the second form of the polymorphic protein to induce an immune response in the first transgenic animal yielding an antibody specific for an epitope characteristic of the second form of the polymorphic protein; and isolating the antibody.

The method preferably further comprises:

isolating from the first transgenic animal a lymphoid cell capable of producing the antibody; and fusing the antibody-producing lymphoid cell with an immortal cell to provide a hybridoma cell which produces the antibody.

The antibody is preferably specific for a polymorphic protein which is a blood group protein, more preferably wherein the blood group protein is gp-Fy protein and the monoclonal antibody is specific for an epitope characteristic of one form of gp-Fy protein.

The invention also includes a method for making an antibody, comprising:

constructing a transgenic animal, preferably a transgenic mouse, to express a first form of an exogenous polymorphic protein encoded by a first allele of a gene encoding the protein;

immunizing the transgenic animal with a peptide comprising an epitope characteristic of a second form of the polymorphic protein to induce an immune response in the transgenic animal yielding an antibody specific for the epitope; and isolating the antibody.

Preferably the method further comprises isolating from the transgenic animal a lymphoid cell capable of producing the antibody. Still more preferably the method further comprises fusing the isolated antibody-producing lymphoid cell with an immortal cell to provide an antibody-producing hybridoma cell.

Preferably, the polymorphic protein is expressed on a cell membrane, e.g., a blood group protein, such as gp-Fy protein. Preferably, the polymorphic protein is a human polymorphic protein.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein:

FIGS. 3A and 3B together constitute a schematic illustration of the Duffy genomic DNA sequence (FY*B) used to produce transgenic mice.

DETAILED DESCRIPTION OF THE PREFERRED EMBODIMENTS

Figure 1:
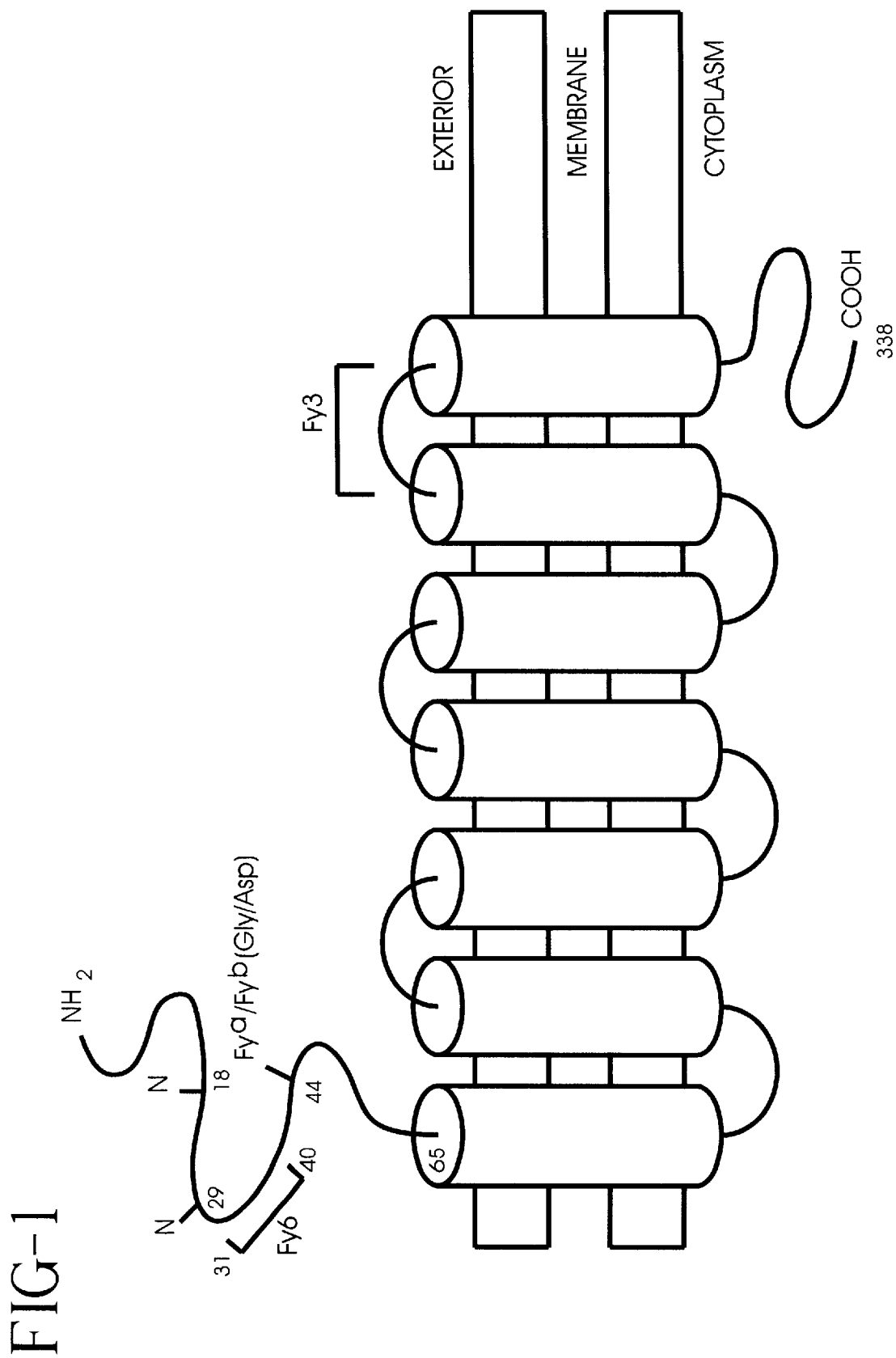
FIG. 1 is a diagram of the proposed topography of the Duffy glycoprotein within the red cell membrane.

The present invention is directed to a method of making antibodies having pre-defined specificity for one form of a polymorphic protein. The invention permits the manufacture of monoclonal antibodies (MAbs) with pre-defined specificities, including MAbs that have eluded production using established protocols despite aggressive efforts in many laboratories. In particular, several specificities to blood group antigens are needed to replace the deceasing supplies of human polyclonal antibodies including, for example: anti-$Fy^a$, anti-$Fy^b$, anti-S, anti-e, anti-$Kp^a$ and anti-$Js^a$.

The experience of cloning the gene encoding the Duffy (gp-Fy) protein, of determining the molecular basis of the $Fy^a/Fy^b$ polymorphism, of producing transgenic mice whose red blood cells (RBCs) express the human $Fy^b$ antigen, have been found to make the Duffy polymorphism an ideal system in which to produce MAbs. Our development of MAbs anti-$Fy^a$ and anti-$Fy^b$ constitute a model system which demonstrates the general utility of using transgenic mice to develop MAbs for any polymorphism which is carried on a protein whose gene has been cloned and the molecular basis of which has been determined. Thus, a comprehensive range of MAbs can now be made as blood typing reagents, as tools for the investigation of biological function, and as possible therapeutic applications.

The polymorphic protein used in the method can be any protein having two or more immunologically differentiable forms. Generally, each form of the protein is encoded by an allele of the same gene. Thus, for any gene where two (or more) alleles are known and are recognized as defining polymorphism in the expressed gene products, the method of the invention can be used to generate monoclonal antibodies against epitopes defined by the polymorphism, if such exist. The protein, therefore, is a protein which is at least potentially recognizable as non-self by an animal which does not express the particular protein.

The protein is preferably a protein which is expressed on or in a cell membrane, such as a cell surface antigen, e.g., a receptor, an enzyme, etc. One highly preferred protein is the Duffy antigen, also known as the gp-Fy protein, having a polymorphism characterized by gp-Fy$^a$ and gp-Fy$^b$ expressed proteins. The Duffy polymorphism is described in U.S. application Ser. No. 08/140,797, filed on Oct. 21, 1993, and in U.S. application Ser. No. 08/749,543, filed on Nov. 15, 1996, the entire disclosures of which are incorporated by reference herein.

Other blood group antigens can be used to develop monoclonal antibodies according to the method of the invention. For example, the Rh group and the Kell group are known to include allelic polymorphisms which can be exploited according to the invention. Other blood group proteins or red blood cell membrane proteins having known polymorphism are shown in Table 1.

those proteins against which monoclonal antibody cannot be routinely made by conventional methods.

The invention can further be used to identify polymorphisms in proteins where none has been previously identified. For example, if two or more alleles of a gene are known, each encoding a different form of the protein in question, then the transgenic method can be used to determine whether such polymorphism corresponds to epitopic differences sufficient to induce an immune reaction. Similarly, other mechanisms associated with protein polymorphism, e.g., differential splicing at the mRNA level, can be studied and exploited by means of the invention. The induction of a cell secreting antibody specifically reactive with the protein used as the putative immunogen provides substantive evidence of epitopic difference. A utility of such an approach is found in the ability to generate information about a protein where conventional immunological characterization reagents and methods fail to yield adequate information. For example, conventional hydropathy analysis may produce ambiguity of interpretation as to whether a difference in primary structure lies within or without the cell membrane. The production of a monoclonal antibody having specificity for one form of the protein but not another would constitute evidence of a difference in extracellular conformation.

TABLE 1

Some Red Cell Blood Group Antigens with One Amino Acid Substitution

| Blood Group System | Antigen Polymorphism | Codon | Residue No. | Amino Acid |
|---|---|---|---|---|
| MNS | s⇒S | ATG⇒ACG | 29 | Met⇒Thr |
|  | ENEH⇒Hut | ACG⇒AAG | 28 | Thr⇒Lys |
|  | ENEH⇒VW | ACG⇒ATG | 28 | Thr⇒Met |
| Rh | C⇒c | TCT⇒CCT | 103 | Ser⇒Pro |
|  | E⇒e | CCT⇒GCT | 226 | Pro⇒Ma |
|  | Tar (−)⇒(+) | CTX⇒CCX | 110 | Leu⇒Pro |
| Kell | k⇒K | ACG⇒ATG | 193 | Thr⇒Met |
|  | Kp$^b$⇒Kp$^a$ | CGG⇒TGG | 281 | Arg⇒Trp |
|  | Kp$^b$⇒Kp$^c$ | CGG⇒CAG | 281 | Arg⇒Gln |
|  | Js$^b$⇒Ja$^a$ | CTC⇒CCC | 597 | Leu⇒Pro |
|  | K11⇒K17 | GTC⇒GCC | 302 | Val⇒Ala |
|  | U1$^a$(−)⇒(+) | GAT⇒GTA | 494 | Glu⇒Val |
|  | K17(−)⇒(+) | GTC⇒GCC | 302 | Val⇒Ala |
|  | K1 (−)⇒(+) | ACG⇒ATG | 193 | Thr⇒Met |
| Duffy | Fy$^b$⇒Fy$^a$ | GAT⇒GGT | 44 | Asp⇒Gly |
| Diego | Di$^a$⇒Di$^b$ | CCX⇒CTX | 854 | Pro⇒Leu |
|  | Wr$^b$⇒Wr$^a$ | GAG⇒AAG | 658 | Glu⇒Lys |
|  | Wd(−)⇒(+) | GTG⇒ATG | 557 | Val⇒Met |
|  | Rb$^a$ (−)⇒(+) | CCA⇒CTA | 548 | Pro⇒Leu |
|  | WARR(−)⇒(+) | ACX⇒ATX | 552 | Thr⇒Ile |
|  | ELO(−)⇒(+) | CGG⇒TGG | 432 | Arg⇒Trp |
|  | Fr$^a$(−)⇒(+) | GAG⇒AAG | 480 | Glu⇒Lys |
|  | Wu(−)⇒(+ | GGC⇒GCC | 565 | Gly⇒Ala |
|  | Bp $^a$(−⇒(+) | ACA⇒AAA | 569 | Asn⇒Lys |
|  | Hg $^a$(−)⇒(+) | CGT⇒TGT | 656 | Arg⇒Cys |
|  | Mo $^a$(−)⇒(+) | CGT⇒CAT | 656 | Arg⇒His |
| Yt | Yt $^a$⇒Yt$^b$ | CAC⇒AAC | 322 | His⇒Asn |
| Colton | Co $^a$⇒Co$^b$ | GCG⇒GTG | 45 | Ala⇒Val |
| Landsteiner-Wiener | LW $^a$⇒LW$^b$ | CAG⇒CGG | 70 | Gln⇒Arg |
| Cromer | Cr$^a$ (+)⇒(−) | GCA⇒CCA | 193 | Ala⇒Pro |
|  | Tc$^a$⇒Tc$^b$ | CGT⇒CTT | 18 | Arg⇒Leu |
|  | WES$^b$⇒WES$^a$ | CTX⇒CGX | 48 | Leu⇒Arg |
| Indian | In$^b$⇒In$^a$ | CGG⇒CCG | 26 | Arg⇒Pro |

The invention, therefore permits the generation of panels of blood typing antibodies (e.g., hemagglutination reagents) against any or all of the various expressed epitopes of any or all of these blood group proteins. But the invention is useful in general to develop monoclonal antibodies against any polymorphic cell surface membrane protein, especially The cloning and sequencing of the human Duffy gene has enabled numerous utilities related to characterizing the normal physiological role of the gp-Fy protein as well as the abnormal role of the protein as a malarial binding ligand. Of particular interest for the present invention, the knowledge of the molecular basis of the Duffy blood group polymorphism enables the construction of transgenic animals to express heterologous Duffy protein. Various transgenic techniques are known, and certain of these techniques can yield heritability of the transgene. See, e.g., Pinkert et al. (1995) for an overview of these techniques, and the documents cited there for greater detail. For example, the invention takes advantage of transgenic mammals transformed by integration of an expressible transgene comprising a heterologous Duffy-related nucleic acid sequence into the genome of the mammal. Such transgenic animals express a Duffy protein normally expressed in erythrocytes of another species, preferably a human Duffy protein.

The animal used to create the transgenic model can be any species, but is preferably a mammal, for example, mice, rats, goats, sheep, pigs, cats, dogs, rabbits, horses or another mammal. Mice are particularly preferred. Moreover, it is preferred that the animal to be transformed be inbred to have a high degree of genetic uniformity between individuals, so that no interfering immune response is generated upon introduction of the cells from one animal into another. Numerous strains of inbred animals, most notably mice, are commercially available. The skilled artisan will appreciate advantages derived from the animal having a relatively well characterized genome, and especially a well characterized immune system. It is further preferred that the autologous gene or genes, if any, which is(are) evolutionarily related to the heterologous gene be at least partially understood at the molecular level.

By employing transgenic animals expressing only one form of a polymorphic protein, the method of the invention ensures that the only immunological difference between cells of the transgenic mouse and the cells or protein used as the immunogen will be the polymorphism. This approach virtually guarantees that any immune response raised by the transgenic mouse will raise an immune response directed solely against the single polymorphic difference. This approach has the potential of allowing production of MAbs that are currently unavailable, as well as MAbs specific for antigens that require the milieu of the cell membrane to be expressed.

To date, no MAb anti-$Fy^a$ or anti-$Fy^b$ have been produced. Clinically significant antibodies of both specificities have been described (Giblett 1977; Badakere et al. 1970; Freisleben 1951; Beattie 1988) and it is important to be able to type donor and patient blood for the corresponding antigens in the pre-transfusion setting. Attempts to make specific MAb anti-$Fy^a$ and anti-$Fy^b$ have included injection of mice or rabbits with human RBCs, enriched Duffy protein or synthetic peptides, but these methods have been unsuccessful. Use of the purified Duffy protein or peptides as immunogens has resulted in production of antibodies to the Duffy protein but not to the polymorphism. These findings suggest that the $Fy^a$ and $Fy^b$ antigens are expressed only if the Duffy protein is within the milieu of the RBC membrane.

Thus, to resolve this ambiguity, the present method can be used to make $Fy^a$ transgenic mice, with RBCs from these mice being injected into existing $Fy^b$ transgenic mice. RBCs from the $Fy^b$ transgenic mice are injected into the $Fy^a$ transgenic mice. This cross-immunization protocol, i.e., immunization between allelic transgenic mice, provides an exquisite means by which to make MAbs with specificities not currently available. Indeed, following this approach, a more comprehensive range of MAb specificities can be made.

The $Fy^a$ antigen was first discovered on erythrocytes in 1950 using an antibody (called anti-$Fy^a$) in the serum of a multitransfused hemophiliac patient (Cutbush 1950). Just a year later, its antithetical antibody, anti-$Fy^b$ was reported (Ikin et al. 1951). The Duffy blood group system has expanded modestly over years, however, intense interest in Duffy was triggered when the gene encoding Duffy glycoprotein (gp-Fy) was cloned in 1993 (Chaudhuri et al. 1993), and the role of gp-Fy in the RBC membrane was elucidated (Neote et al. 1994; Horuk et al. 1993; Iwamoto et al. 1996).

Gp-Fy, which is predicted to have seven transmembrane α-helices, is encoded by a gene on the long arm of chromosome 1 (Donahue et al. 1968). The protein has an apparent molecular mass of $M_r$ 35,000 to 43,000 on a polyacrylamide gel. The antigens $Fy^a$ and $Fy^b$, located on the N-terminal extracelluar domain of gp-Fy (FIG. 1) (Chaudhuri et al. 1995; Iwamoto et al. 1995; Mallinson et al. 1995), define four phenotypes in this blood group system: Fy(a+b−), Fy(a−b+), Fy(a+b+) and Fy(a−b−). In whites, the first three phenotypes are commonly observed, and Fy(a−b−) individuals are extremely rare. However, the Fy(a−b−) phenotype among blacks is frequent in African-Americans and reaching almost 100% in people from some areas of West Africa (Race et al. 1975). In Fy(a−b−) individuals of African descent, the absence of Duffy antigens is associated with an absence of Duffry glycoprotein in the RBC membrane due to a single nucleotide substitution of GATA to GACA in the erythroid promoter (Tournamille et al. 1995). Thus, Duffy mRNA was detected in many other tissues in both Duffy positive and Duffy negative individuals (Neote et al. 1994; Iwamoto et al. 1996; Chaudhuri et al 1995).

Anti-$Fy^a$ and anti-$Fy^b$ are usually IgG molecules and are of variable clinical significance. Mild hemolytic transfusion reactions have been attributed to examples of these antibodies. Two other antibodies, anti-Fy3 and murine MAb anti-Fy6 bind to the Duffy glycoprotein (Albrey et al. 1971; Nichols et al. 1987). Fy3 and Fy6 are present on all RBCs except those of the Fy(a−b−) phenotype. Using a MAb anti-Fy3, the Fy3 antigen has been shown to reside on the last extracellular loop of the gp-Fy protein (FIG. 1) (Lu et al. 1995). A MAb anti-Fy6, produced by immunizing mice with pooled red cells (Riwom et al. 1994), binds to the N-terminal extracellular region between amino acids 31 and 40 of the gp-Fy protein (Hausman et al. 1996). The distribution of Fy6 on RBCs of non-human primates differs from $Fy^a$, $Fy^b$ and Fy3 (Nichols et al. 1987). MAb anti-Fy6 has been invaluable in the isolation of gp-Fy (Riwom et al. 1994; Chaudhuri et al. 1989).

Apart from the fact that $Fy^a$ and $Fy^b$ are immunogenic in humans and are frequently involved in blood transfusion, the biochemical and functional characterization of the gp-Fy is of major importance. In addition to cloning the gene encoding gp-Fy by Chaudhuri and coworkers (described in U.S. Application Ser. No. 08/140,797, filed on Oct. 21, 1993), the functions of gp-Fy as a chemokine receptor and its involvement in the process of invasion of human RBCs by malarial parasites *Plasmodium vivcax* and *P. knowlesi* (a simian parasite) were elucidated (Chaudhuri et al. 1989; Miller et al. 1975; Miller et al. 1976; Barnwell et al. 1989). Horuk and coworkers (1993) showed that gp-Fy acts as a receptor for chemokines responsible for such processes as cell interaction, cell growth and inflammation, namely interleukin-8 (IL-8), melanoma growth stimulatory activity (MGSA), RANTES and monocyte chemotactic protein 1 (MCP-1). However, there is no subsequent signal transduction demonstrated upon binding. It has been suggested that gp-Fy absorbs excess cell-signaling molecules (Darbonne et al. 1991). Despite the intensive work performed on the gp-Fy, the role of Duffy antigens in invasion by malaria parasites and in the binding to chemokines is not clear. What is clear is that structural information on the gp-Fy is needed to understand the process of the interaction between the merozoite or chemical ligands and its RBC membrane receptor. Once anti-Fy$^a$ and anti-Fy$^b$ MAbs are available, they can be used to further investigate the specific topology of the gp-Fy protein that contributes to the Fy$^a$/Fy$^b$ epitopes.

The genes encoding Fy$^a$ and Fy$^b$ antigens have been cloned. Transgenic mice have been constructed, whose RBCs express the human Fy(a–b+) phenotype, by injecting genomic DNA into mouse zygotes. This knowledge can be used to generate transgenic mice expressing the human Fy(a+b–) phenotype. The offspring of these transgenic mice are expected to carry either human Fy$^a$ or Fy$^b$ antigens on their RBCs. Blood cells isolated from one group of transgenic mice are used to immunize the other group. This approach overcomes the observed problem that certain antigens can only induce an immune response by their close relatives, but not by lower species. Furthermore, it significantly limits the contamination of antibodies obtained by injection of human RBCs into mice. Perhaps most significantly, the only difference between the RBCs of the transgenic mouse being immunized and the transgenic mice RBCs being used as the immunogen is the Duffy antigen. Thus, it is highly probable that the mouse will mount an immune response to the Fy$^a$ or Fy$^b$ polymorphism. After immunization, the spleen of the immunized mice is isolated, fused to myeloma cells and processed by conventional hybridoma technique to select hybrids secreting anti-Fy$^a$ and anti-Fy$^b$. Such MAbs will be useful in the replacement of human anti-serum reagents in the practice of blood typing and in the investigation of the topology and function of the Duffy glycoprotein.

In addition, study on the capability of stimulation of immune response with the truncated protein or the intact cells will provide important topological information of gp-Fy. Nonetheless, the transgenic mice constructed will be extremely useful to elucidate the functions and biological role of the Duffy protein, and that would serve as an excellent animal model to develop any possible therapeutic treatments for chemokine disorders or the infection of malarial parasite in the third world.

The following examples are provided to assist in a further understanding of the invention. The particular materials and conditions employed are intended to be further illustrative of the invention and are not limiting upon the reasonable scope thereof.

EXAMPLE 1

Preparation of Transgenic Mice Expressing gp-Fy$^b$ Protein

Figure 2:
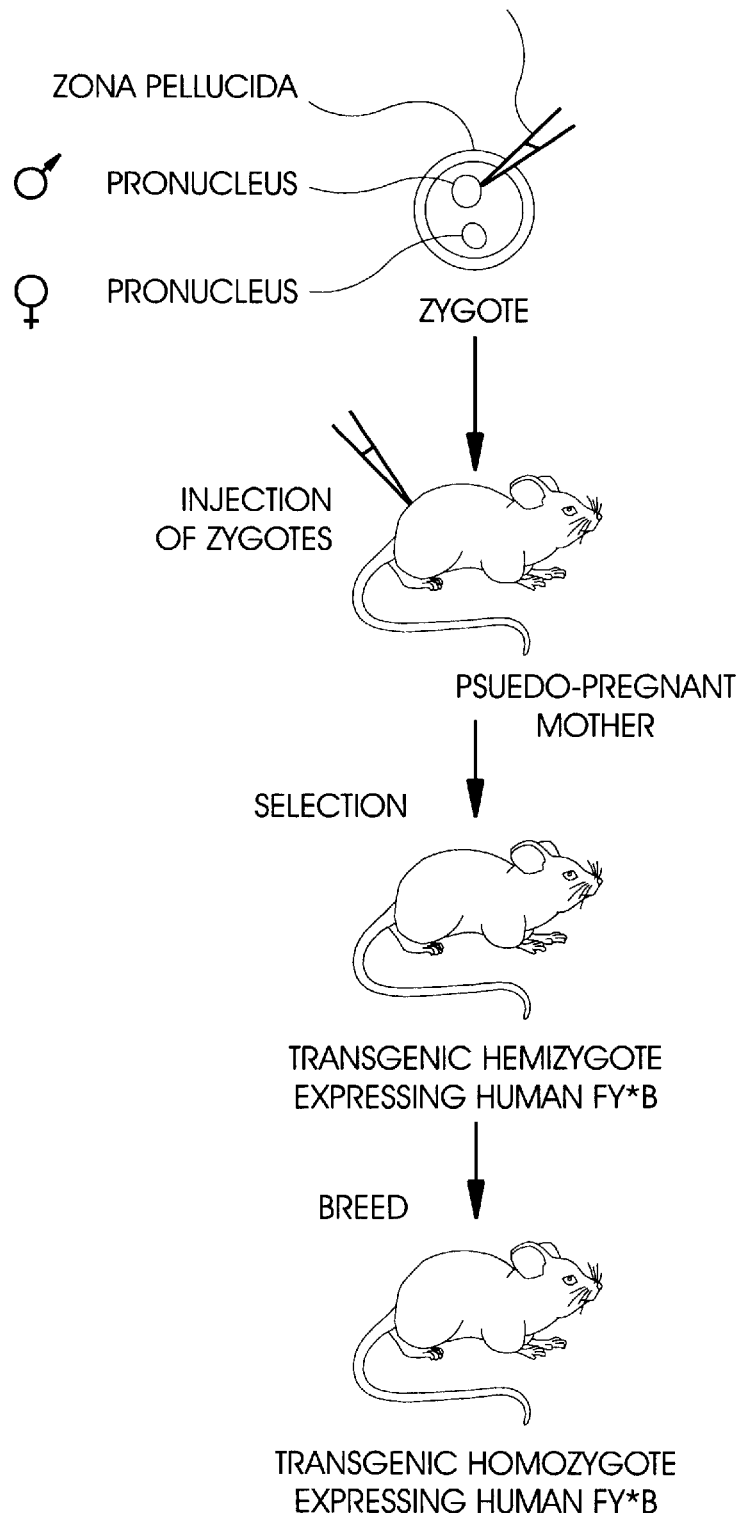
FIG. 2 is a schematic illustration of a method of constructing transgenic mice expressing FY*B.

Transgenic mice have been constructed to express the human Duffy gp-Fy$^b$ antigen using a method substantially in accordance with that illustrated in FIG. 2. A 3523 bp genomic DNA fragment containing FY*B coding sequence and ~1.5 kb upstream and ~1 kb downstream flanking sequences (SEQ ID NO: 1; see also FIGS. 3A and 3B) was amplified by the polymerase chain reaction using FY-specific primers (sense: 5-CTGCAGGGGTAGATGCCCTTTCTC-3 (SEQ ID NO:2); antisense: 5-GAATTCCAAGCAGAAGATGAATC-3 (SEQ ID NO:3)). The amplified fragment was cloned in the pBluescript vector (Strategene). Plasmid DNA was purified by two-round centrifugation in CsCl gradients. The fragment containing the inserted genomic FY*B gene was excised by appropriate restriction enzymes and separated on a gel followed by DNA purification. The pure DNA fragment was reconstituted to a concentration of approximately 5 μg/mL and was used to construct transgenic mice.

The purified DNA fragment was micro-injected into the male pronucleus of fertilized eggs of the B6/CBA F1 mouse (Jackson Laboratory, Bar Harbor, Me.), which had been removed from the oviducts of a female mouse that had mated the night before. The zygotes with the insertion were transferred to the oviducts of 0.5-day pseudo-pregnant females and allowed to develop into embryos. Ten females became pregnant, producing 60 pups.

Figure 4:
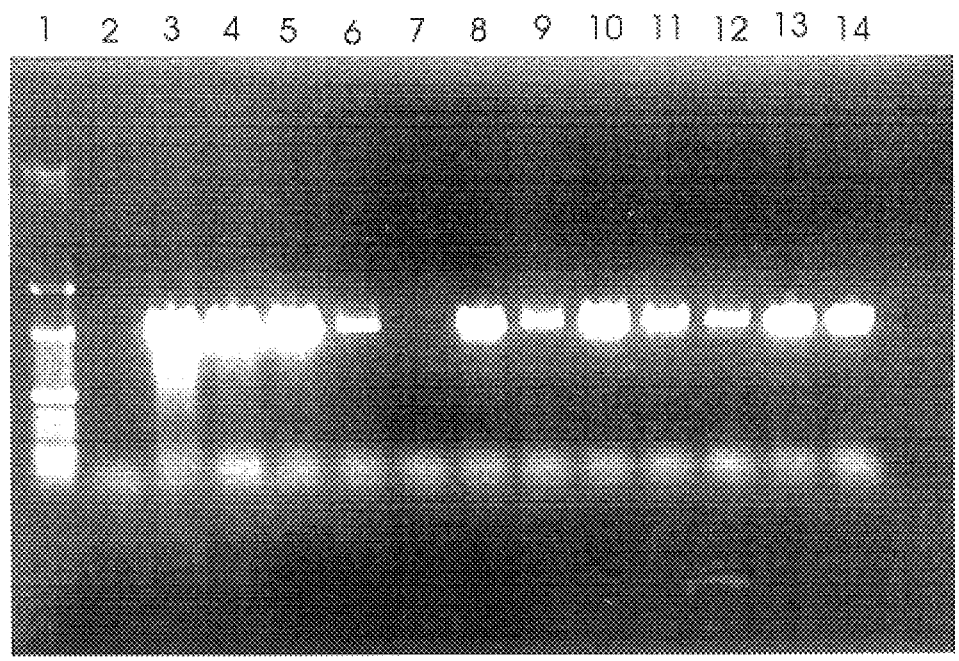
FIG. 4 is a digitized image of PCR amplification products derived from Duffy genomic DNA sequence showing integration into the genome of transgenic mice.

Four weeks after birth, DNA was prepared from tail clips of each baby animal using proteinase K digestion and ethanol precipitation. The DNA was tested for FY sequence integration by dot blot hybridization with a probe derived from the Duffy genomic DNA or by PCR amplification using FY-specific primers. In the PCR, 200 ng of the genomic DNA was amplified with the Duffy-specific primers with Taq polymerase. The PCR reaction was carried out for 30 cycles as follows: 30 s at 94° C., 30 s at 65° C., and 3 min at 72° C. Ten microlit (10 μL) of the reaction mixture was run on a 1% agarose gel, using a 1 kb DNA marker, with a non-transgenic mouse sample as a control. FIG. 4 shows representative PCR results, with a DNA marker (lane 1), DNA from a non-transgenic mouse control (lane 2), and DNA samples from 12 transgenic mice (lanes 3–14). The dot blot hybridization and PCR amplification showed that 11 out of the 60 mice (18% transduction rate) had successful integration of the human Duffy genomic DNA into their chromosome, and more than one copy of FY was observed (data not shown).

Expression of the exogenous gene was examined by hemagglutination. Serological studies were performed by collecting blood from each animal showing successful integration of human Duffy DNA by puncture of the orbital plexus under an anesthetized condition. The isolated RBCs were tested for the presence of human Fy$^b$ antigen by hemagglutination using murine MAbs anti-Fy3, anti-Fy6, and human anti-Fy$^b$. Of the 11 transgenic mice having the Duffy gene incorporated, RBCs from four mice showed the expression of the expected cognate antigens. These results are shown in Table 2, below, which summarizes immunological data concerning red cells from the 11 mice as compared to human red cells.

TABLE 2

| Erythrocytes | anti-Fy3 | Anti-Fy6 | Anit-Fy$^b$ | PCR |
| --- | --- | --- | --- | --- |
| Human | ++ | ++ | ++ | Positive |
| Mouse #1 | ++++ | ++ | ++ | Positive |
| Mouse #2 | ++++ | ++ | ++ | Positive |
| Mouse #3 | – | – | – | Positive |
| Mouse #4 | – | – | – | Positive |
| Mouse #5 | ++ | ++ | ++ | Positive |
| Mouse #6 | – | – | – | Positive |
| Mouse #7 | +++ | + | ++ | Positive |
| Mouse #8 | – | – | – | Positive |
| Mouse #9 | – | – | – | Positive |
| Mouse #10 | – | – | – | Positive |
| Mouse #11 | – | – | – | Positive |

These data indicate that not all of the integration of FY*B gene occurred at the chromosomal site which is being actively transcribed. However, approximately 7% of the transfected animals actively transcribed FY and synthesized (expressed) the Duffy Fy$^b$ protein. Furthermore, it is demonstrated that the integrated DNA sequence contains all of the information necessary for Duffy promoter activity and its expression in erythroid specific manner. The red cells of the transgenic mice are serologically identical to a Duffy-positive human having Fy(a–b+) erythrocytes. These agglutination data imply that the expressed human Duffy protein was folded onto the mouse RBC membrane preserving its native (i.e., human) conformational structure and antigenic sites.

It is worth noting that random integration of the Duffy genomic DNA into mouse chromosome demonstrably works well in expression of the Duffy protein. Even so, targeted integration into an appropriate chromosome may be necessary for producing desired transgenic animals in other cases. Such targeted transformation can be accomplished by conventional methods, and given the information provided herein is within the skill of the artisan.

EXAMPLE 2

Construction of Transgenic Mouse Expressing Human $Fy^a$ Antigen

The method described in Example 1 is directly adaptable for the construction of a transgenic animal expressing the $Fy^a$ antigen. In this case, the genomic DNA of FY*A are either amplified from an individual of Fy(a+b–) phenotype, as described above, or obtained by performing site-directed mutagenesis at nucleotide 131 of the open reading frame (ORF) ($A^{131} \rightarrow G$). The $Fy^a$ and $Fy^b$ antigens differ as a result of single nucleotide difference ($G^{131}$ or A) encoding amino acids $Gly^{44}$ ($Fy^a$) or Asp ($Fy^b$) in the N-terminal extracellular domain of the Duffy glycoprotein. A vector is constructed containing the FY*A DNA, and mice are transfected. The resulting transformed mice express human $Fy^a$ on their red cell surfaces, having a conformation suitable for producing an agglutination reaction identical to that of native human $Fy^a$. Once transformed, the transgenic mice can be bred to obtain the homozygous transgenic mice, and further bred to produce a stock of animals having the same DNA insertion.

EXAMPLE 3

Preparation of Soluble Peptides That Express $Fy^a$ or $Fy^b$ Antigens

To examine if the extracellular N-terminal 65 amino acids are sufficient to stimulate an immune response to $Fy^a$ or $Fy^b$ antigens, Duffy-based peptides can be synthesized using recombinant DNA technology. The fragment encoding the N-terminal hydrophilic domain of the gp-Fy is amplified by using appropriate primers (see FIGS. 3A and 3B) with a purification tag of six histidine and a proteolytic site in front of it. To ensure that the truncated gp-Fy is immunogenic, the recombinant peptide might require conjugation to an inert carrier (MAP core) or dimerized through a recombination PCR procedure. The resulting PCR fragment is sequenced to ensure the perfect amplification and then inserted into an eukaryotic expression vector. As $Fy^b$ has been successfully expressed in K562 cells, a human erythroleukemic cell line (Chaudhuri et al. 1994), the eukaryotic vector can be transiently transfected into K562 cells by calcium phosphate technique. The supernatant containing the truncated version of gp-Fy is harvested between 48 to 72 hours after transfection and eluted through either an ion exchange column or an affinity column with the conjugation of murine MAb anti-Fy6. The purified protein can be injected into the transgenic mice as the appropriate immunogen.

EXAMPLE 4

Immunization of $Fy^a$ and $Fy^b$ Transgenic Mice Using Recombinant Peptides Recombinant $Fy^a$ peptide is injected into the $Fy^b$ transgenic mice prepared in Example 1 using a standard immunization protocol (Rudbach et al. 1995). Likewise, recombinant $Fy^b$ peptide is injected into the $Fy^a$ transgenic mice prepared according to Example 2. Serum is collected and examined for the production of anti-$Fy^a$ and anti-$Fy^b$, respectively. Since the human gp-Fy has become one of the native proteins on the RBCs of these transgenic mice during embryonic development, immunization with human-origin antigen will likely produce a stronger immune response in them as compared to that in the original nontransgenic mice. The immunogenicity of the recombinant peptide is optimized through the use of appropriate adjuvants to yield highly quantitative and qualitative antibodies.

If specific antibody is produced in response to the injected peptide, the monoclonal hybridoma technique is employed as described below. Otherwise, if the soluble peptide does not induce an immune response, this may indicate that the epitopes of $Fy^a$ and $Fy^b$ are associated with other regions (e.g., the extracellular loops) of the Duffy protein or with other membrane proteins. This would suggest that the entire Duffy molecule with a mature conformation on the RBC membrane is needed to create the proper epitope for immunization. Thus, the RBCs of the transgenic mice would be the best immunogen. Moreover, in order to evaluate whether the transgenic mouse that expresses the native human Duffy protein is indeed a better host for immunization, the same procedure can be performed using an original untreated strain.

EXAMPLE 5

Immunization Using Transgenic Mice RBCs Expressing $Fy^a$ or $Fy^b$

Figure 5:
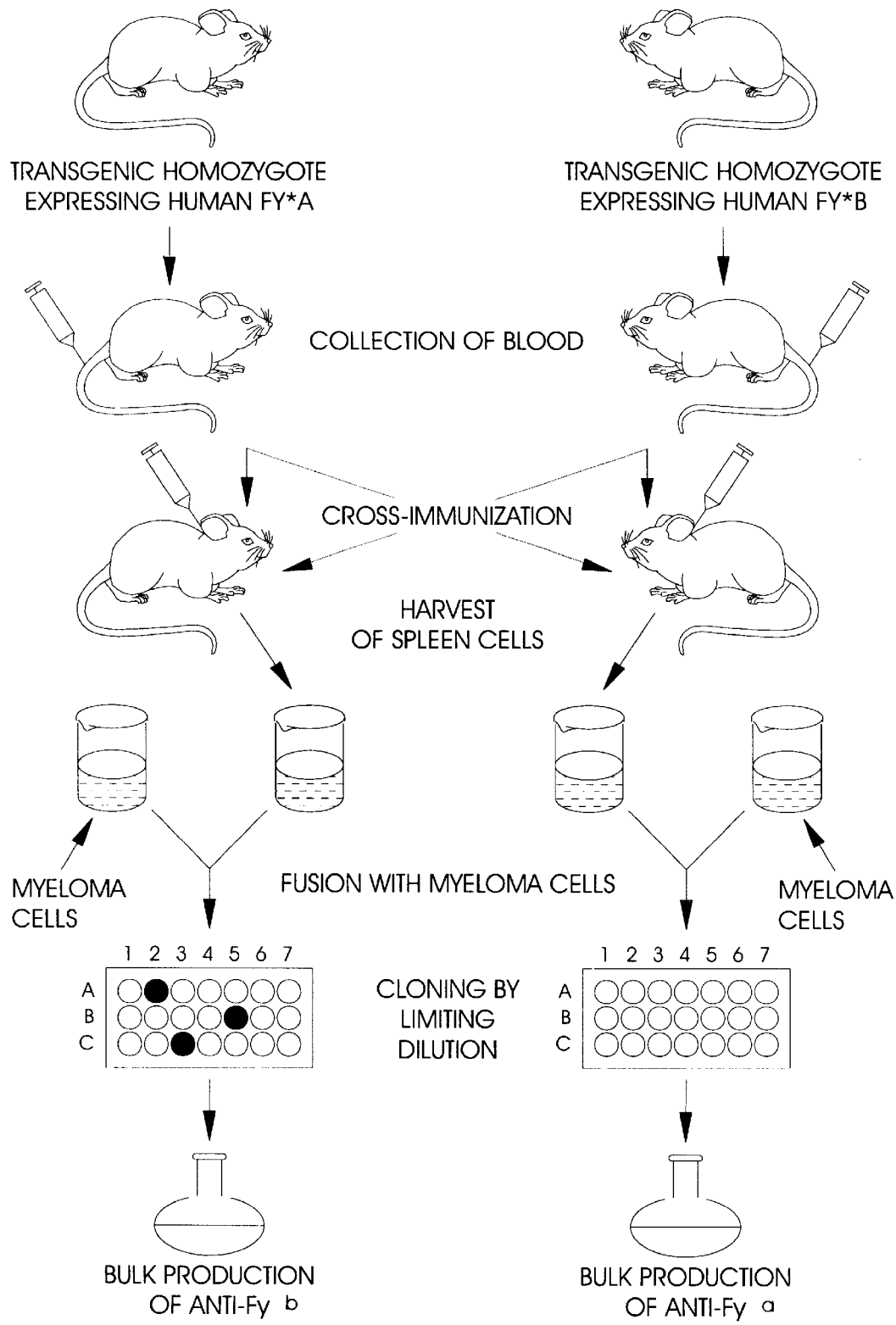
FIG. 5 is a schematic illustration of a method of producing monoclonal antibodies by the transgenic animal/hybridoma technique of the invention.

Once the transgenic strains of $Fy^a$ and $Fy^b$ mice are established, a cross-immunization procedure is performed generally in conformity with the method illustrated in FIG. 5. The RBCs isolated from each mouse strain are injected subcutaneously and intravenously into the mice of their counter group. We have shown that $Fy^b$ antigens are expressed on the transgenic mouse RBCs as indicated by specific human antiserum (Table 2). As these two sources of RBCs only differ in the expression of either $Fy^a$ antigen or $Fy^b$ antigen, and not any other antigenic sites of the Duffy protein (e.g., Fy3 and Fy6) or other RBC-borne antigens, the polymorphic sites of $Fy^a$ or $Fy^b$ are the only target to produce antibody. This results in a greater chance of making anti-$Fy^a$ and anti-$Fy^b$ since the presumably higher immunogenic epitopes to mouse immune system are unrecognizable in this protocol. This assumption is based on the finding that immunization of mice with RBCs, purified gp-Fy, or synthetic peptides has only resulted in production of antibodies to the gp-Fy and not to the $Fy^a/Fy^b$ polymorphism.

EXAMPLE 6

Immunization of Non-Transgenic Mice with RBCs from a Transgenic $Fy^b$ Mouse Since transgenic mice whose RBCs express human $Fy^b$ antigens are available, the cells of these mice can be used to immunize mice of the same wild type strain. If the non-transgenic mice mount an immune response, the preparation of MAbs can be usefully attempted.

EXAMPLE 7

Fusion and Cloning of the Hybridoma Cells Secreting Anti-$Fy^a/Fy^b$

After final immunization, the mice selected according to satisfactory antibody titers are killed and their spleens are removed. The splenocytes are fused into the mouse myeloma X63-Ag8.653 cells using a standard polyethylene glycol (PEG)/dimethylsulfoxide (DMSO) procedure, followed by HAT selection (Rudbach et al. 1995; Gorny et al. 1994). The mouse myeloma used for fusion is usually a HAT-sensitive variant of the Balb/c-derived myeloma. Although the spleen cell donor is an inbred strain other than Balb/c, the MAb is generated only from cell culture fluids, thereby avoiding the histocompatibility problem. Alternatively, the F1 progeny of a Balb/c:"spleen cell donor" cross, which contains both sets of histocompatibility antigens, can be used to grow the hybridomas.

The supernatant of the hybridoma cells is screened for antibody secretion with antigen-positive and antigen-negative human RBCs by direct hemagglutination or ELISA. Hybridoma cells producing specific antibody are cloned by limiting dilution. The stable cell lines are frozen for future use or expanded in culture for bulk production of antibodies. By this protocol, both IgG and IgM antibodies are obtained.

This result makes possible the use of direct agglutinating monoclonal anti-$Fy^a$ and anti-$Fy^b$ for screening programs to find antigen-negative donors, since currently available reagents require the antiglobulin test and cannot be used to type RBCs with a direct antiglobulin test.

EXAMPLE 8

Evaluation of the Monoclonal Anti-$Fy^a$ and Anti-$Fy^b$

The monoclonal anti-$Fy^a$ and anti-$Fy^b$ are evaluated for their specificity and sensitivity in comparison to the current reagents by using a large number of blood samples from random donors and by testing rare RBCs with known phenotypes, which are commercially available. Standard hemagglutination techniques are used.

EXAMPLE 9

Characterization of the Monoclonal Anti-$Fy^a$ and Anti-$Fy^b$ Antibodies

The nucleotide sequences of variable domains of anti-$Fy^a$ and anti-$Fy^b$ are identified by sequence analysis with specific primers for this region. As the $Fy^a/Fy^b$ antigen is suggested to be involved in the chemokine binding and in the parasite invasion, the obtained information will be extremely useful for design of an immunotherapeutic agent or a "vaccine" for blocking the interactions between the Duffy protein and its ligands or the parasites.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, mentioned in the foregoing specification, are incorporated herein by reference for all that they disclose:

Giblett ER. "Blood group alloantibodies: An assessment of some laboratory practices," *Transfusion* 4:299–308 (1977).

Badakere SS, Bhatia H M. "A fatal transfusion reaction due to anti-Duffy ($Fy^a$) case report," *Indian J Med Sci* 24:562–564 (1970).

Freiesleben E. "Fatal hemolytic transfusion reaction due to anti-$Fy^a$ ('Duffy')," *Acta Path Microbiol Scand* 29:283–286 (1951).

Beattie K M. "The Duffy blood group system: Distribution, serology and genetics," In: Pierce SR, Macpherson CR, eds., *Blood Group Systems. Duffy, Kidd and Lutheran.* American Association of Blood Banks, Arlington, Va., pp. 1–25 (1988).

Landsteiner K. "Über Agglutinationserscheinungen normalen menschlichen Blutes," Klin Wschr14:1132 (1901).

Kohler G, Milstein C. "Continuous cultures of fused cells secreting antibody of predefined specificity," *Nature* 256:495–497 (1975).

Doyle A, Jones T J, Bidwell J L, Bradley B A. "In vitro development of human monoclonal antibody-secreting plasmacytomas," *Human Immunology* 13:199–209 (1985).

Crawford D H, Barlow M J, Harrison J F, Winger L, Huehns E R. "Production of human monoclonal antibody to rhesus D antigen," *Lancet* 1:386–388 (1983).

Cutbush M, Mollison PI, Parkin D M. "A new human blood group," *Nature* 165:188 (1950). Ikin E W, Mourant A K, Pettenkofer H J, Blumenthal G. "Discovery of the expected haemagglutinin anti-$Fy^b$," *Nature* 168:1077–1078 (1951).

Chaudhuri A, Polyakova J, Zbrzezna V, Williams K, Gulati S, Pogo A O. "Cloning of glycoprotein D cDNA, which encodes the major subunit of the Duffy blood group system and the receptor for the *Plasmodium vivax* malaria parasite," *Proc Natl Acad Sci USA* 90:10793–10797 (1993).

Neote K, Mak J Y, Kolakowski L F, Jr., Schall T J. "Functional and biochemical analysis of the cloned Duffy antigen: Identity with the red blood cell chemokine receptor," Blood 84:44–52 (1994).

Horuk R, Chitnis C E, Darbonne W C, et al. "A receptor for the malarial parasite *Plasmodium vivax*: the erythrocyte chemokine receptor," *Science* 261:1182–1184 (1993).

Iwamoto S, Li J, Omi T, Ikemoto S, Kajii E. "Identification of a novel exon and spliced form of Duffy mRNA that is the predominant transcript in both erythroid and postcapillary venule endothelium," *Blood* 87:378–385 (1996).

Donahue R P, Bias W, Renwick J H, McKusick V A. "Probable assignment of the Duffy blood group locus to chromosome I in man," *Proc Natl Acad Sci USA* 61:949–955 (1968).

Chaudhuri A, Polyakova J, Zbrzezna V, Pogo O. "The coding sequence of Duffy blood group gene in humans and simians: Restriction fragment length polymorphism, antibody and malarial parasite specificities, and expression in nonerythroid tissues in Duffy-negative individuals," *Blood* 85:615–621 (1995).

Iwamoto S, Omi T, Kajii E, Ikemoto S. "Genomic organization of the glycophorin D gene: Duffy blood group $Fy^a/Fy^b$ alloantigen system is associated with a polymorphism at the 44-amino acid residue," *Blood* 85:622–626 (1995).

Mallinson G, Soo K S, Schall T J, Pisacka M, Anstee D J. "Mutations in the erythrocyte chemokine receptor (Duffy) gene: The molecular basis of the $Fy^a/Fy^b$ antigens and identification of a deletion in the Duffy gene of an apparently healthy individual with the Fy(a−b−) phenotype," *Br J Haematol* 90:823–829 (1995).

Race R R, Sanger R. *Blood Groups in Man*, 6th Ed., Blackwell, Oxford, England (1975).

Tournamille C, Colin Y, Cartron J-P, Le Van Kim C. "Disruption of a GATA motif in the Duffy gene promoter abolishes erythroid gene expression in Duffy-negative individuals," *Nature Genet* 10:224–228 (1995).

Albrey J A, Vincent EE, Hutchinson J, et al. "A new antibody, anti-Fy3, in the Duffy blood group system," *Vox Sang* 20:29–35 (1975).

Nichols M E, Rubinstein P, Barnwell J, Rodriguez de Cordoba S, Rosenfield R E. "A new human Duffy blood group specificity defined by a murine monoclonal antibody: Immunogenetics and association with susceptibility to *Plasmodium vivax*," *J Exp Med* 166:776–785 (1987).

Lu ZH, Wang Z X, Hadley T J, Hesselgesser J, Horuk R, Peiper S C. "Localization of the Fy3 epitope of the Duffy antigen/receptor for chemokines (DARC) to the third extracellular loop which is not involved in chemokine binding (abstract)" *Blood* 86(Suppl 1):444a (1995).

Riwom S, Janvier D, Navenot J M, Benbunan M, Muller J Y, Blanchard D. "Production of a new murine monoclonal antibody with Fy6 specificity and characterization of the immunopurified N-glycosylated Duffy-active molecule," *Vox Sang* 66:61–67 (1994).

Hausman E, Dzik W, Blanchard D. "The red cell chemokine receptor is distinct from the Fy6 epitope," *Transfusion* 36:421–425 (1996).

Chaudhuri A, Zbrzezna V, Johnson C, et al. "Purification and characterization of an erythrocyte membrane protein complex carrying Duffy blood group antigenicity. Possible receptor for *Plasmodium vivax* and *Plasmodium knowlesi* malaria parasite," *J Biol Chem* 264:13770–13774 (1989).

Miller L H, Mason S J, Dvorak J A, McGinniss M H, Rothman I K. "Erythrocyte receptors for (*Plasmodium knowlesi*) malaria: Duffy blood group determinants," *Science* 189:561–563 (1975).

Miller L H, Mason S J, Clyde D F, McGinniss M H. "The resistance factor to *Plasmodium vivax* in blacks. The Duffy blood group genotype, FyFy," *N Engl J Med* 295:302 (1976).

Barnwell J W, Nichols M E, Rubinstein P. "In vitro evaluation of the role of the Duffy blood group in erythrocyte invasion by *Plasmodium vivax*," *J Exp Med* 169:1795–1802 (1989).

Darbonne W C, Rice G C, Mohler M A, et al. "Red blood cells are a sink for interleukin-8, a leukocyte chemotaxin," *J Clin Invest* 88:1362–1369 (1991).

Chaudhuri A, Zbrzezna V, Polyakova J, Pogo A O, Hesselgesser J, Horuk R. "Expression of the Duffy antigen in K562 cells. Evidence that it is the human erythrocyte chemokine receptor," *J Biol Chem* 269:7835–7838 (1994).

Rudbach J A, Cantrell J L, Ulrich J T. "Methods of immunization to enhance the immune response to specific antigens in vivo in preparation for fusions yielding monoclonal antibodies." In: Davis W C, ed., *Monoclonal Antibody Protocols*. Humana Press, Totowa, N.J., pp. 1–8 (1995).

Gorny M K. "Production of human monoclonal antibodies via fusion of Epstein-Barr virus-transformed lymphocytes with heteromyeloma." In: Cellis JE, ed., *Cell Biology: A Laboratory Handbook*. Academic Press, San Diego, Calif., pp. 276–281 (1994).

Pinkert C A, M H Irwin, and R J Moffatt, "Transgenic animal modeling." In: Myers R A, ed., *Molecular Biology and Biotechnology: A Comprehensive Desk Reference*. VCH Publishers, Inc., New York, pp. 901–907 (1995).

---

What is claimed is:

1. A method of making an antibody, comprising:

constructing a first transgenic mouse whose somatic and germ cells comprise a polynucleotide sequence encoding one human Duffy protein polymorph of either $Fy^a$ or $Fy^b$ and whose somatic cells express either the $Fy^a$ or $Fy^b$ polymorph encoded by the polynucleotide;

constructing a second transgenic mouse whose somatic and germ cells comprise a polynucleotide sequence encoding the human Duffy protein polymorph $Fy^a$ or $Fy^b$ which is not contained in said first transgenic mouse and whose somatic cells express either the $Fy^a$ or $Fy^b$ human Duffy protein polymorph not expressed in said first transgenic mouse, wherein said second transgenic mouse is syngeneic to said first transgenic mouse;

immunizing said first transgenic mouse with cells from said second transgenic mouse to induce an immune response in said first transgenic mouse, wherein a lymphoid cell of said first transgenic mouse produce an antibody specific for an epitope of the human Duffy protein polymorph expressed by the somatic cells of said second transgenic mouse; and isolating the antibody.

2. A method according to claim 1, further comprising isolating from said first transgenic mouse a lymphoid cell capable of producing said antibody.

3. A method according to claim 2, firer comprising fusing said antibody-producing lymphoid cell with an immortal cell to provide an antibody-producing hybridoma cell.

4. A method according to claim 1, wherein the mouse is a B6/CBA F1 mouse.

5. A hybridoma cell that produces antibodies specific to one human Duffy protein polymorph of either $Fy^a$ or $Fy^b$, prepared by a method comprising:

constructing a first transgenic mouse whose somatic and germ cells comprise a polynucleotide sequence encoding one human Duffy protein polymorph of either $Fy^a$ or $Fy^b$ and whose somatic cells express either the $Fy^a$ or $Fy^b$ polymorph encoded by the polynucleotide;

constructing a second transgenic mouse whose somatic and germ cells comprise a polynucleotide sequence encoding the human Duffy protein polymorph $Fy^a$ or $Fy^b$ which is not contained in said first transgenic mouse and whose somatic cells express either the $Fy^a$ or $Fy^b$ human Duffy protein polymorph not expressed in said first transgenic mouse, wherein said second transgenic mouse is syngeneic to said first transgenic mouse;

immunizing said first transgenic mouse with cells from said second transgenic mouse to induce an immune response in said first transgenic mouse, wherein the lymphocytes of said first transgenic mouse produce an antibody specific for an epitope of the human Duffy protein polymorph expressed by the somatic cells of said second transgenic mouse;

isolating from said first transgenic mouse a lymphoid cell which produces said antibody; and fusing said antibody-producing lymphoid cell with an immortal cell to provide a hybridoma cell that produces antibodies specific to one of the human Duffy protein polymorphs $Fy^a$ or $Fy^b$.

6. A method of making an antibody, comprising:

constructing a transgenic mouse whose somatic and germ cells comprise a polynucleotide sequence encoding one human Duffy protein polymorph of either $Fy^a$ or $Fy^b$ and whose somatic cells express either the $Fy^a$ or $Fy^b$ polymorph encoded by the polynucleotide;

immunizing said transgenic mouse with the human Duffy protein polymorph of either $Fy^a$ or $Fy^b$ which is not expressed by said transgenic mouse to induce an immune response in said transgenic mouse, wherein a lymphoid cell of said transgenic mouse produces an antibody specific for an epitope of the human Duffy protein polymorph not expressed by said transgenic mouse; and isolating the antibody.

7. A method according to claim 6, further comprising isolating from said transgenic mouse a lymphoid cell capable of producing said antibody.

8. A method according to claim 7, further comprising fusing said antibody-producing lymphoid cell with an immortal cell to provide an antibody-producing hybridoma cell.

9. A method according to claim 6, wherein the other Duffy protein polymorph is expressed on a cell membrane.

10. A method according to claim 6, wherein said transgenic mouse is a B6/CBA F1 mouse.

* * * * *

UNITED STATES PATENT AND TRADEMARK OFFICE
CERTIFICATE OF CORRECTION

PATENT NO. : 6,054,632
DATED : April 25, 2000
INVENTOR(S) : Marion E. Reid

It is certified that error appears in the above-identified patent and that said Letters Patent is hereby corrected as shown below:

In Column 21, Line 38, change "A method according to Claim 2, firer... "to--A method according to Claim 2, further..--.

Signed and Sealed this

Tenth Day of April, 2001

Attest:

NICHOLAS P. GODICI

*Attesting Officer*  Acting Director of the United States Patent and Trademark Office

UNITED STATES PATENT AND TRADEMARK OFFICE
CERTIFICATE OF CORRECTION

| | | |
|---|---|---|
| PATENT NO. | : 6,054,632 | Page 1 of 1 |
| APPLICATION NO. | : 08/749527 | |
| DATED | : April 25, 2000 | |
| INVENTOR(S) | : Marion E. Reid | |

It is certified that error appears in the above-identified patent and that said Letters Patent is hereby corrected as shown below:

Column 1, line 5, insert the following:

--This invention was made with government support under grant DA010342 awarded by the National Institutes of Health. The government has certain rights in the invention.--

Signed and Sealed this
Seventh Day of August, 2012

David J. Kappos
*Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 3523 nucleotides
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO:1:

```
CTGCAGGGGT AGATGCCCTT TCTCTCTGCT GGCCAGCTCT GCCCCTCAGT          50

GAGAAACTTT ACATATTGCT AAGATGCCTG GCCAATGAAA CAGTTCCAGA         100

GACTTTATGT CCCCAGTAGA AATATGAATA GAAATCACCC TGTGCTCAAT         150

GGTCCCATTT TAAAATATGC TGTCCCATTG TCCCCTAGAG CCTATCTTAA         200

CTTGTCAGAC CATGTATTCC ACTTCATATG CAAGAGGCAT GCACTGAGCC         250

CATAGGTGGC TAGGCAAACA CCCAATAGCT CCCTGAAATG GCTTCATTAT         300

GGAGGCTCGA CAGCCACCCC AACCCTCCCA CTCTCACACT GAAACACCCA         350

GACCTAGAGA TAGCTAGACA CACCCAGACA CCCGCCAAGC CCCTCACATA         400

CAGATATGTG CACAATGATA CACAGCAAAT GTACACAGAG TTCAGTACAC         450
```

-continued

```
ACAAAGAGCT CACGCCCACG TGCACACACC CCTCAGTTGG GACAGAGTTG        500

ACCACCACCA CCTTTCTCCC AAACACATGG CTTTGGAACT GCCTTTCCTT        550

GGATCCAGTT CAAGGGGATG GAGGAGCAGT GAGAGTCAGC CGCCCTTCCA        600

CTCCAATTTC CCAGCACCTC CCTTATCTCT GCCTCACAAG TCACCCAGCC        650

CCCCTCTCTT CCTTCCTTGT GCTTGAAGAA TCTCTCCTTG CTGGAAAGCC        700

CCCTGTTTTC TCAATCTCCC TTTCCACTTC GGTAAAATCT CTCCTTGCTG        750

GAAAGCCCCC TGTTTTCTCA ATCTCCCTTT CCACTTCGGT AAAATGCCCA        800

CTTTCTGGTC CCCACCTTTT TCCTGAGTGT AGTCCCAACC AGCCAAATCC        850

AACCTCAAAA CAGGAAGACC CAAGGCCAGT GACCCCCATA GGCCTGAGGC        900

TTGTTGCAGG CAGTGGGCGT GGGGTAAGGC TTCCTGATGC CCCCTGTCCC        950

TGCCCAGAAC CTGATGGCCC TCATTAGTCC TTGGCTCTTA TCTTGGAAGC       1000

ACAGGCGCTG ACAGCCGTAC CAGCCCTTCT GTCTGCGGGC CTGAACCAAA       1050

CGGTGCCATG GGGAACTGTC TGCACAGGGT GAGTATGGGG CCAGGCCCCA       1100

GAGTCCCTTA TCCCTATGCC CCTCATTTCC CCTGCTGTTT GCCCCTCAGT       1150

CTTTATATCT CTTCCTTTTC CTCCTCATCT TTTCTCCCTT CCTGCTTTTT       1200

TCCTCTTCCT TCAAAGTCTT TTTCCTTTTC TCCTTCCTAT GCTAGCCTCC       1250

TAGCTCCCTC TTGTGTCCCT CCCTTTGCCT TTGAGTCAGT TCCATCCTGG       1300

TCTCTTGGTG CCTTTCCTTC TGACCTTGCA CTGCTCCTCC AGCCCCAGCT       1350

GCCCTGGCTT CCCCAGGACT GTTCCTGCTC CGGCTCTTCA GGCTCCCTGC       1400

TTTGTCCTTT TCCACTGTCC GCACTGCATC TGACTCCTGC AGAGACCTTG       1450

TTCTCCCACC GCACCTTCCT CTCTGTCCTC CCCTCCCACC TGCCCCTCAG       1500

TTCCCAGGAG ACTCTTCCGG TGTAACTCTG ATGGCCTCCT CTGGGTATGT       1550

CCTCCAGGCG GAGCTCTCCC CCTCAACTGA GAACTCAAGT CAGCTGCAGT       1600

TCGAAGATGT ATGGAATTCT TCCTATGGTG TGAATGATTC CTTCCCAGAT       1650

GGAGACTATG ATGCCAACCT GGAAGCAGCT GCCCCCTGCC ACTCCTGTAA       1700

CCTGCTGGAT GACTCTGCAC TGCCCTTCTT CATCCTCACC AGTGTCCTGG       1750

GTATCCTAGC TAGCAGCACT GTCCTCTTCA TGCTTTTCAG ACCTCTCTTC       1800

CGCTGGCAGC TCTGCCCTGG CTGGCCTGTC CTGGCACAGC TGGCTGTGGG       1850

CAGTGCCCTC TTCAGCATTG TGGTGCCCGT CTTGGCCCCA GGGCTAGGTA       1900

GCACTCGCAG CTCTGCCCTG TGTAGCCTGG GCTACTGTGT CTGGTATGGC       1950

TCAGCCTTTG CCCAGGCTTT GCTGCTAGGG TGCCATGCCT CCCTGGGCCA       2000

CAGACTGGGT GCAGGCCAGG TCCCAGGCCT CACCCTGGGG CTCACTGTGG       2050

GAATTTGGGG AGTCCGTGCC CTACTGACAC TGCCTGCTAC CCTGGCCAGT       2100

GGTGCTTCTG GTGGACTCTG CACCCTGATA TACAGCACGG AGCTGAAGGC       2150

TTTGCAGGCC ACACATACTG TAGCCTGTCT TGCCATCTTT GTCTTGTTGC       2200

CATTGGGTTT GTTTGGAGCC AAGGGGCTGA AGAAGGCATT GGGTATGGGG       2250

CCAGGCCCCT GGATGAATAT CCTGTGGGCC TGGTTTATTT TCTGGTGGCC       2300

TCATGGGGTG GTTCTAGGAC TGGATTTCCT GGTGAGGTCC AAGCTGTTGC       2350

TGTTGTCAAC ATGTCTGGCC CAGCAGGCTC TGGACCTGCT GCTGAACCTG       2400
```

-continued

| | |
|---|---|
| GCAGAAGCCC TGGCAATTTT GCACTGTGTG GCTACGCCCC TGCTCCTCGC | 2450 |
| CCTATTCTGC CACCAGGCCA CCCGCACCCT CTTGCCCTCT CTGCCCCTCC | 2500 |
| CTGAAGGATG GTCTTCTCAT CTGGACACCC TTGGAAGCAA ATCCTAGTTC | 2550 |
| TCTTCCCACC TGTCAACCTG AATTAAAGTC TACACTGCCT TTGTGAAGCG | 2600 |
| GGTGGTTTCT TATTTTGTCT GGGGAGAAGA AGGAGAATGG AGAGAGAGAC | 2650 |
| ATTTTTATGT CAGACTTTCT TGCCAGTGTC TGCTTCTATA GCTGGCTTGG | 2700 |
| GAAGAAGGTG AATGATGAAT AAATACCCTC AGGGTACACA GATGTTCTCT | 2750 |
| TGAGGTGTGG GGTCAGGCCA TCTCAAGGGA GAAGAGAAGA GGAACTAGAG | 2800 |
| CATGAGGGGA GTCATTAAAC CAAAAAAAAC AGAAGGGATG GCTTAGCTGG | 2850 |
| AAAAAAAGCT GTTCTGGGAA GCAAATGGAA TAGGAACTCA AACTGAGAGA | 2900 |
| TAAACAGTGA AGAGTGATGA CAAAGCCCAG AGCAATACCA CCTCCCCCTG | 2950 |
| TCCAACCTGC CCAGCCTCTG TCTTCTGTCT CCTCTCTGGC TTTGTTTAGT | 3000 |
| GATTAGGACA GTGGTGGGGA AGGTGAAAGA AGCATCCCAG GGGATGTTAC | 3050 |
| TCAGTTCAGG GAACATATCA AGGTAATTTA AAAAGCCACT TCCTGGGAGT | 3100 |
| CATCTCTCCC AGGTTCCTCA GCATGACCTG AATGTGTGTG TGTGCGTGTG | 3150 |
| TGTGTGTGTG TGTACACATC TGTTTCTCGA TCTGTTAGAA TCTACCTTTA | 3200 |
| TGTTAGATGT ATGCATGTAA AAACATATGT CCACCCATGA GCTTGCATCT | 3250 |
| CTGCTAGCAC CTGAACTGCG ACACCTGTGC GTGTGCACTG ACTTTTCTCA | 3300 |
| GGACCCAAAC CCCCACTCAA TTCTGCACTC ATCCCTGTTC ACAGGATATA | 3350 |
| GAATCGGGAT TTATGACTCA CTCCTTACCC AAATGAGTTT TCTTTACCCT | 3400 |
| GGTTTTTAAG CCTAGTCTTT TCTGTGTAGG ATGTGTGGAG GGAAGAAAAG | 3450 |
| ATCAAGAAGT TGTGAGGGGT GGAGAAACTT GAAGGGGGAG GCCCTGATTT | 3500 |
| GATTCATCTT CTGCTTGGAA TTC | 3523 |

(2) INFORMATION FOR SEQ ID NO:2:

(i) SEQUENCE CHARACTERISTICS:
        (A) LENGTH: 24 nucleotides
        (B) TYPE: nucleic acid
        (C) STRANDEDNESS: double
        (D) TOPOLOGY: linear (ii) MOLECULE TYPE: other nucleic acid (iii) SEQUENCE DESCRIPTION: SEQ ID NO:2:

| | |
|---|---|
| CTGCAGGGGT AGATGCCCTT TCTC | 24 |

(2) INFORMATION FOR SEQ ID NO:3:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear

```
(ii) MOLECULE TYPE:  other nucleic acid (xi) SEQUENCE DESCRIPTION: SEQ ID NO:3:

GAATTCCAAG CAGAAGATGA ATC                                    23
```